(12) United States Patent
Hovan et al.

(10) Patent No.: US 6,781,695 B2
(45) Date of Patent: Aug. 24, 2004

(54) LIGHT SOURCE FOR OPEN-PATH GAS MONITORING

(75) Inventors: Richard Hovan, Doylestown, PA (US); Stuart F. Metcalfe, South Yorkshire (GB); Derek D. Stuart, Derbyshire (GB)

(73) Assignee: Land Instruments International, Inc., Newtown, PA (US)

( * ) Notice: Subject to any disclaimer, the term of this patent is extended or adjusted under 35 U.S.C. 154(b) by 262 days.

(21) Appl. No.: 09/964,242

(22) Filed: Sep. 26, 2001

(65) Prior Publication Data

US 2003/0038940 A1 Feb. 27, 2003

(30) Foreign Application Priority Data

Aug. 24, 2001 (GB) .............................. 0120588

(51) Int. Cl.[7] .......................... G01N 21/00; H01L 33/00; F21V 11/00; G01J 5/02
(52) U.S. Cl. ...................... 356/437; 362/555; 362/558; 362/227; 362/257; 250/339.13; 73/1.06
(58) Field of Search ................................ 356/437–438; 353/20; 396/199; 362/555, 558, 84, 227, 257; 250/338.5, 339.13; 73/1.02, 1.06, 23.3

(56) References Cited

U.S. PATENT DOCUMENTS 4,381,153 A * 4/1983 Bohl et al. .................. 356/437

| 4,637,719 | A | | 1/1987 | Herman |
|---|---|---|---|---|
| 4,640,621 | A | * | 2/1987 | Rose .......................... 356/434 |
| 5,028,790 | A | | 7/1991 | McGowan et al. |
| 5,517,314 | A | * | 5/1996 | Wallin ........................ 356/437 |
| 5,617,212 | A | * | 4/1997 | Stuart ........................ 356/438 |
| 6,404,984 | B1 | * | 6/2002 | Parvulescu et al. ........... 396/16 |
| 6,476,911 | B1 | * | 11/2002 | Rose .......................... 356/337 |
| 6,558,021 | B2 | * | 5/2003 | Wu et al. .................... 362/249 |

FOREIGN PATENT DOCUMENTS

| EP | 0022 506 | 1/1981 |
|---|---|---|
| EP | 0848 243 | 6/1998 |

OTHER PUBLICATIONS

American Society for Testing and Materials, "Standard Practive for Opacity Monitor Manufacturers to Certify Conformance with Design and Performance Specifications" (D 6216–98) (provided by applicant).*

British Patent Office Search Report under Section 17(5) dated May 31, 2002.

* cited by examiner

Primary Examiner—Russell Adams
Assistant Examiner—Magda Cruz
(74) Attorney, Agent, or Firm—Caesar, Rivise, Bernstein, Cohen & Pokotilow, Ltd.

(57) ABSTRACT

An improved light source for use in an opacity monitor (transmissometer) that reduces the variation in light intensity across a projected light beam to enable a more accurate and stable method for measuring the opacity of gases in a stack/duct, especially at low values (e.g., <10%) of opacity while operating within specific performance requirements.

11 Claims, 6 Drawing Sheets

LIGHT SOURCE FOR OPEN-PATH GAS MONITORING

RELATED APPLICATIONS

This application claims priority from British patent application No. 0120588.9 filed on Aug. 24, 2001 under 35 U.S.C. §119.

FIELD OF THE INVENTION

The invention pertains to a light source used for open-path gas monitoring, particularly for the measurement of the smoke and dust content of stack gases, but also applicable to the measurement of particulates in the atmosphere.

BACKGROUND OF INVENTION

The standard method for continuous emissions measurement of particulates in stacks and ducts is optical transmissometry. The measured quantity is opacity, defined as the fraction of transmitted light which is lost in transmission through a medium.

Figure 1:
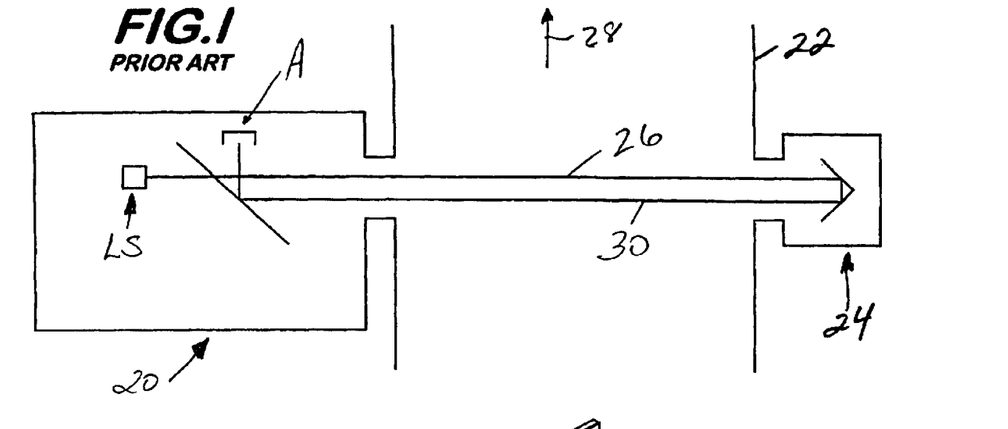
FIG. 1 is a functional diagram of a prior art transmissometer coupled to a stack.

One example of a device that measures opacity, known as a transmissometer, is the Land Combustion Model 4500mkII opacity monitor which has been used for a number of years to measure the opacity of gases in stacks and ducts. A functional diagram of the Model 4500mkII is shown in FIG. 1 wherein the Model 4500mkII consists of two main units: a transceiver 20 mounted on one side of a stack/duct 22 and a passive retroreflector 24 mounted on the other side. A light source LS in the transceiver 20 projects a beam of light 26 along the transceiver's optical axis 27 across the duct 22, through the dust/smoke in the open path 28 of the gas/smoke 29 (FIG. 2) to the retroreflector 24 which returns a reflected light beam 30 to an analyzer A in the transceiver 20. The analyzer A then compares the intensity of the returned radiation with that measured under clear-stack conditions in order to calculate the opacity and then displays this opacity value at a remote location (e.g., a data recorder, not shown). Also see U.S. Pat. No. 5,617,212 (Stuart), whose entire disclosure is incorporated by reference herein, for a detailed description of how the analyzer A calculates the opacity.

Figure 2:
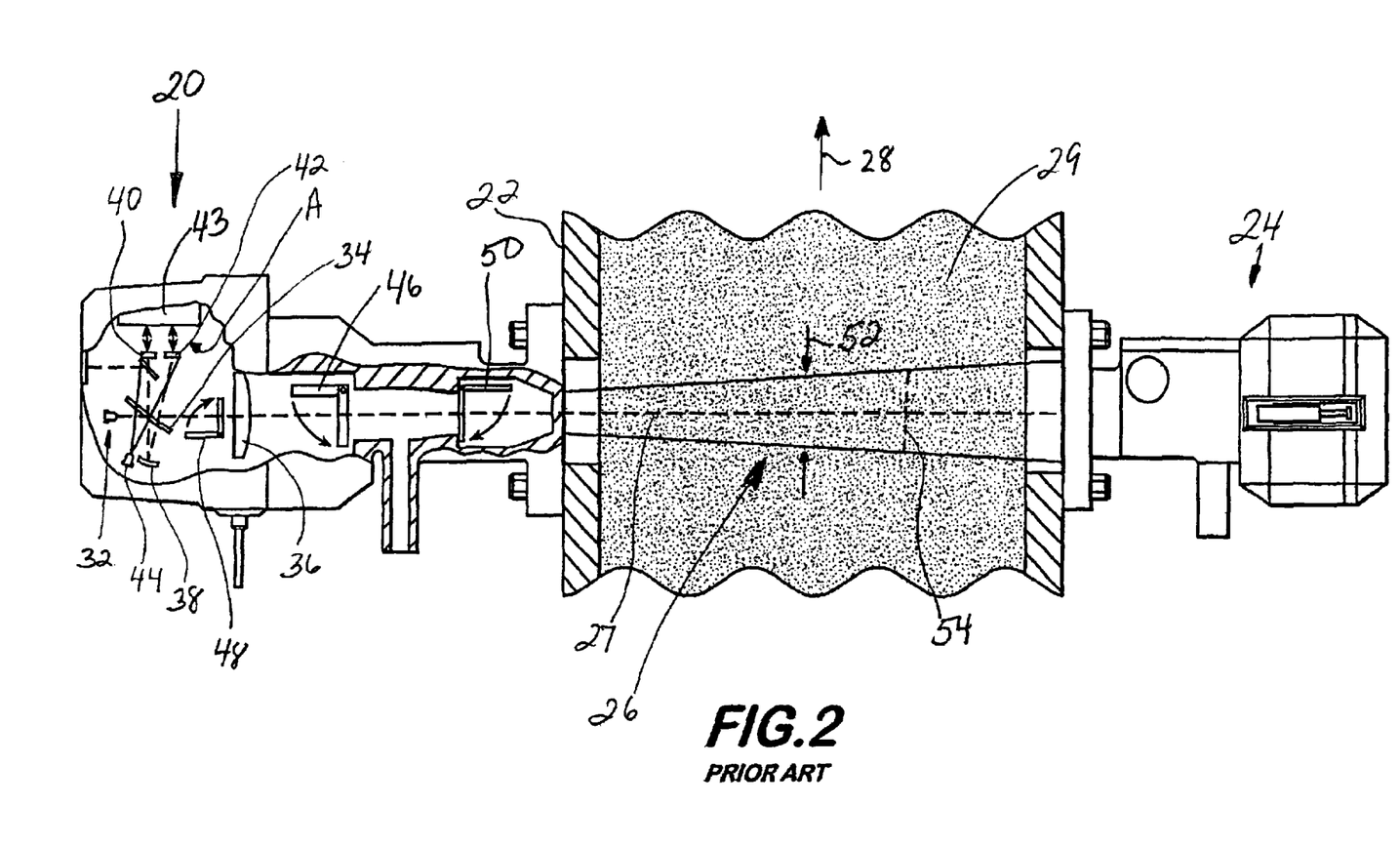
FIG. 2 is a side view, shown in partial cross-section, of the prior art transmissometer of FIG. 1.

FIG. 2 shows the Model 4500mkII mounted to the stack/duct 22 and depicts the internals of the transceiver 20. In particular, the light source LS of the transceiver 20 comprises an LED (light emitting diode) 32. The transceiver 20 also comprises a beamsplitter 34, a collimating lens 36, a folding mirror 38, and the analyzer A which comprises a measurement detector 40, a reference detector 42 and a processor 43 (e.g., Hitachi H8/500 microprocessor). Additional components include a flood LED 44 for drift correction, an automatic zero 46 and span 48 devices and a fail-safe shutter 50. It should be understood that the transmissometer is autocollimated meaning that the return light 30 from the retroreflector 24 is along the same path as the projected beam 26. External electrical power (e.g., 110VAC @ 60 Hz), not shown, is provided to the transceiver 20 for energizing the electrical components.

The divergence 52 of the projected light beam 26 means that the retroreflector 24 returns only a portion of the projected light 26. Any change in alignment, (e.g., because of temperature changes, wind, settling, etc.) in the stack/duct 22 walls, results in a different portion of the projected beam 26 falling on the retroreflector 24. Moreover, because the projected beam 26 is not perfectly homogeneous, i.e., the light intensity varies across the projected beam (see line 54), a change in alignment results in a change in light intensity. This change is wrongly interpreted by the analyzer A as a change in the opacity of the stack/duct 22 gases.

Errors are also introduced where an opacity monitor (transmissometer) with an inhomogeneous light beam is calibrated in the laboratory and then installed on the stack/duct 22. In this case, failure to perfectly reproduce the device's optical alignment between the laboratory and the duct results in a signal offset. This offset is, in many cases, the dominant source of error in the measurement. As a consequence, the detection limit of the opacity monitor may be set by this offset.

A number of factors affect the homogeneity of the projected beam 26, including the precision and cleanliness of the optical components used. However, the principal factor is usually the inhomogeneity of the light source LS. There are a number of factors which make the pattern of light from an LED inhomogeneous. Some of these are symmetrical about the optical axis of the LED and some are not. This is especially so when a LED source is used, since the electrical contact to the center of the die results in a dark spot in the middle of the beam 26.

One way of producing a homogeneous light source is to use an integrating sphere, such as that described in "A Guide to Integrating Sphere Theory and Applications" by Labsphere. However, an integrating sphere is both bulkier and more expensive than the present invention.

The limitations of the present state of the art are reflected in ASTM (American Society for Testing and Materials) Standard Practice for Opacity Monitor Manufacturers to Certify Conformance with Design and Performance Specifications D6216-98 (1998) which is incorporated by reference into U.S. 40 C.F.R. §60, Appendix B, EPA Performance Specification 1, and which concerns the use of opacity monitors for regulatory applications at opacity levels of 10% or higher. However, where detecting opacity levels of less than 10% is important, e.g., in the steel industry, no performance specification currently exists for the use of opacity monitors to ensure compliance with opacity limits below 10%.

Thus, there remains a need for a transmissometer that can minimize the inhomogeneity of the light source and can therefore detect opacity levels below 10% while operating within specific performance requirements.

SUMMARY OF THE INVENTION

A light source for use in an opacity monitor for measuring the opacity of gases in an open path of gases wherein the light source reduces the variation in light intensity across a beam of light projected therefrom.

A light source adapted for use in open path gas monitoring wherein the light source generates a homogeneous light beam.

An opacity monitor for measuring the opacity of gases in an open path of gases wherein opacity is defined as the fraction of transmitted light which is lost in transmission through the open path of gases. The opacity monitor comprises: an optical transmitter for projecting a light beam across the open path of gases using a light source that reduces the variation in light intensity across the projected beam; a reflector for reflecting a portion of the projected light beam back towards the optical transmitter through the open path gas of gases; an analyzer for detecting the portion of the projected light beam and calculating the opacity of the gases; and wherein the optical monitor detects opacities less than 10 percent while operating within specific performance requirements (e.g., all the requirements of ASTM D6216-98, including amendments to specific portions of ASTM D6216-98 to ensure compliance with opacity limits below 10%, such as thermal stability, insensitivity to ambient light, zero and span calibration, measurement of output resolution, calibration error, optical alignment indicator, calibration device value and repeatability, and insensitivity to supply voltage variations).

An opacity monitor for measuring the opacity of gases in an open path of gases wherein opacity is defined as the fraction of transmitted light which is lost in transmission through the open path of gases. The opacity monitor comprises: an optical transmitter having a light source that projects a homogeneous light beam across the open path of gases; a reflector for reflecting a portion of the projected homogeneous light beam back towards the optical transmitter through the open path gas of gases; an analyzer for detecting the portion of the projected homogeneous light beam and calculating the opacity of the gases; and wherein the optical monitor detects opacities less than 10 percent while operating within specific performance requirements (e.g., all the requirements of ASTM D6216-98, including amendments to specific portions of ASTM D6216-98 to ensure compliance with opacity limits below 10%, such as thermal stability, insensitivity to ambient light, zero and span calibration, measurement of output resolution, calibration error, optical alignment indicator, calibration device value and repeatability, and insensitivity to supply voltage variations).

A method for reducing the variation in light intensity across a beam of light projected from a light source used in an opacity monitor. The method comprises the steps of: (a) providing a plurality of light emitting diodes (LEDs), each having a respective optical axis and each emitting respective light beams; (b) arranging the plurality of LEDs at a predetermined angular orientation with respect to each other and aligning each of the optical axes to be parallel to each other; and (c) positioning an optical diffuser at a predetermined distance away from the plurality of LEDs for mixing and reflecting the respective light beams to form the beam of light having a reduced variation in light intensity.

A method for reducing the variation in light intensity across a beam of light projected from a light source used in an opacity monitor. The method comprises the steps of: (a) providing a plurality of light emitting diodes (LEDs), each having a respective optical axis and each having symmetrical and asymmetrical inhomogeneities in respective light beams emanating from each LED; (b) minimizing the symmetrical and asymmetrical inhomogeneities in the respective light beams by: (1) orienting the plurality of LEDs within in a common plane; and (2) positioning an optical diffuser at a predetermined distance away from the plurality of LEDs to mix and reflect the respective light beams to form the beam of light having the reduced variation in light intensity across the beam of light.

A method for measuring the opacity of gases in an open path of gases wherein opacity is defined as the fraction of transmitted light which is lost in transmission through the open path of gases. The method comprises the steps of: (a) projecting a light beam across the open path of gases using a light source that reduces the variation in light intensity across the projected beam; (b) reflecting a portion of the projected light beam; (c) detecting and analyzing the portion of the portion of the projected light beam; (d) detecting opacities less than 10 percent while operating within specific performance requirements (e.g., all the requirements of ASTM D6216-98, including amendments to specific portions of ASTM D6216-98 to ensure compliance with opacity limits below 10%, such as thermal stability, insensitivity to ambient light, zero and span calibration, measurement of output resolution, calibration error, optical alignment indicator, calibration device value and repeatability, and insensitivity to supply voltage variations).

DETAILED DESCRIPTION OF THE PREFERRED EMBODIMENTS

Figure 3:
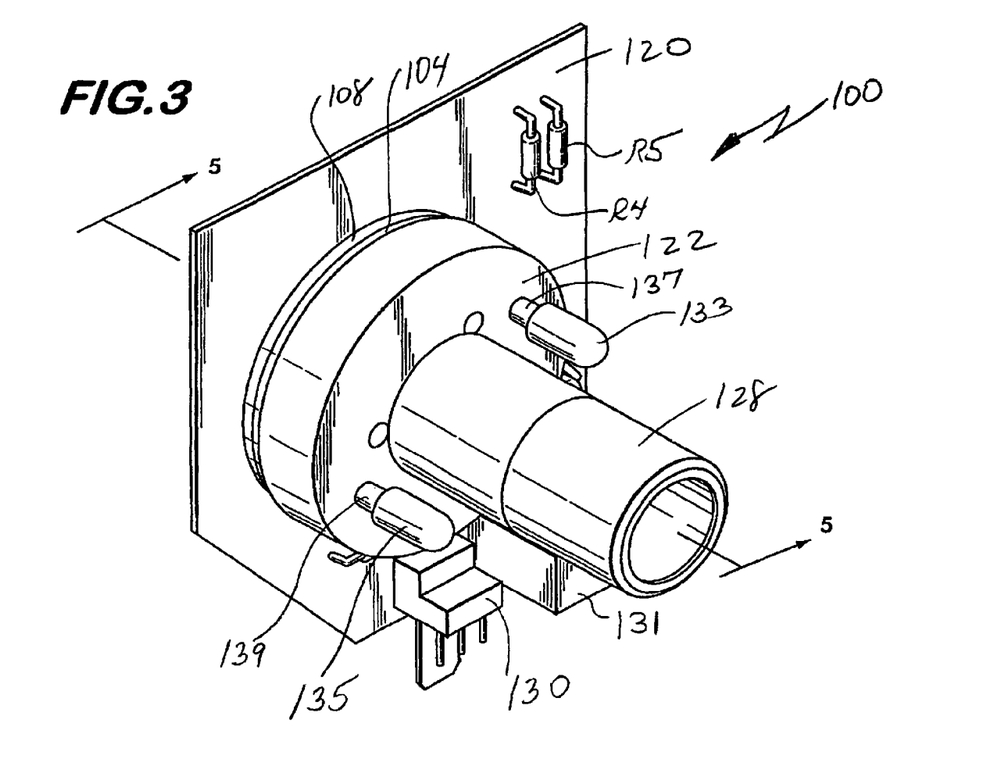
FIG. 3 is an isometric view of the light source of the present invention.

Referring now in detail to the various figures of the drawing wherein like reference characters refer to like parts, there is shown at 100 in FIG. 3, a light source which provides improved light beam homogeneity compared to other light sources used in conventional stack/duct gas analyzers. The result of utilizing this improved light source 100 is a transmissometer analyzer which is more tolerant of optical misalignment than previous designs, and is therefore able to make accurate measurements at very low levels of opacity (e.g., less than 10%).

It should be understood that the light source 100 described herein, and as will be discussed in detail below, replaces the light source LS (e.g., LED 32) described earlier with respect to FIGS. 1–2. However, in all other aspects, e.g., the beamsplitter 34, the collimating lens 36, etc., of the transceiver portion 20 of the transmissometer which utilizes the present invention 100 is similar and is not discussed any further.

Figure 4:
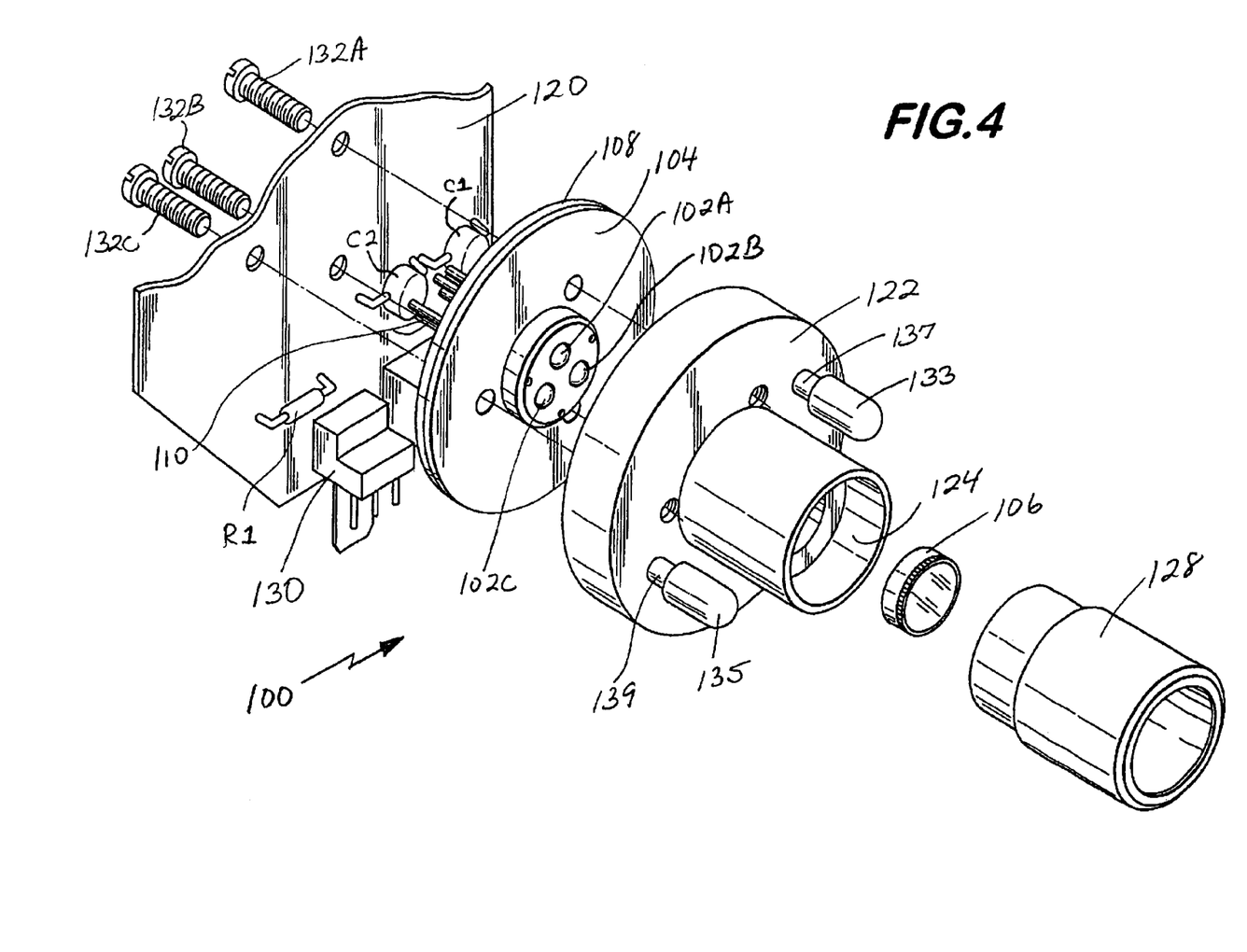
FIG. 4 is an exploded view of the light source of FIG. 3.
Figures 5, 6:
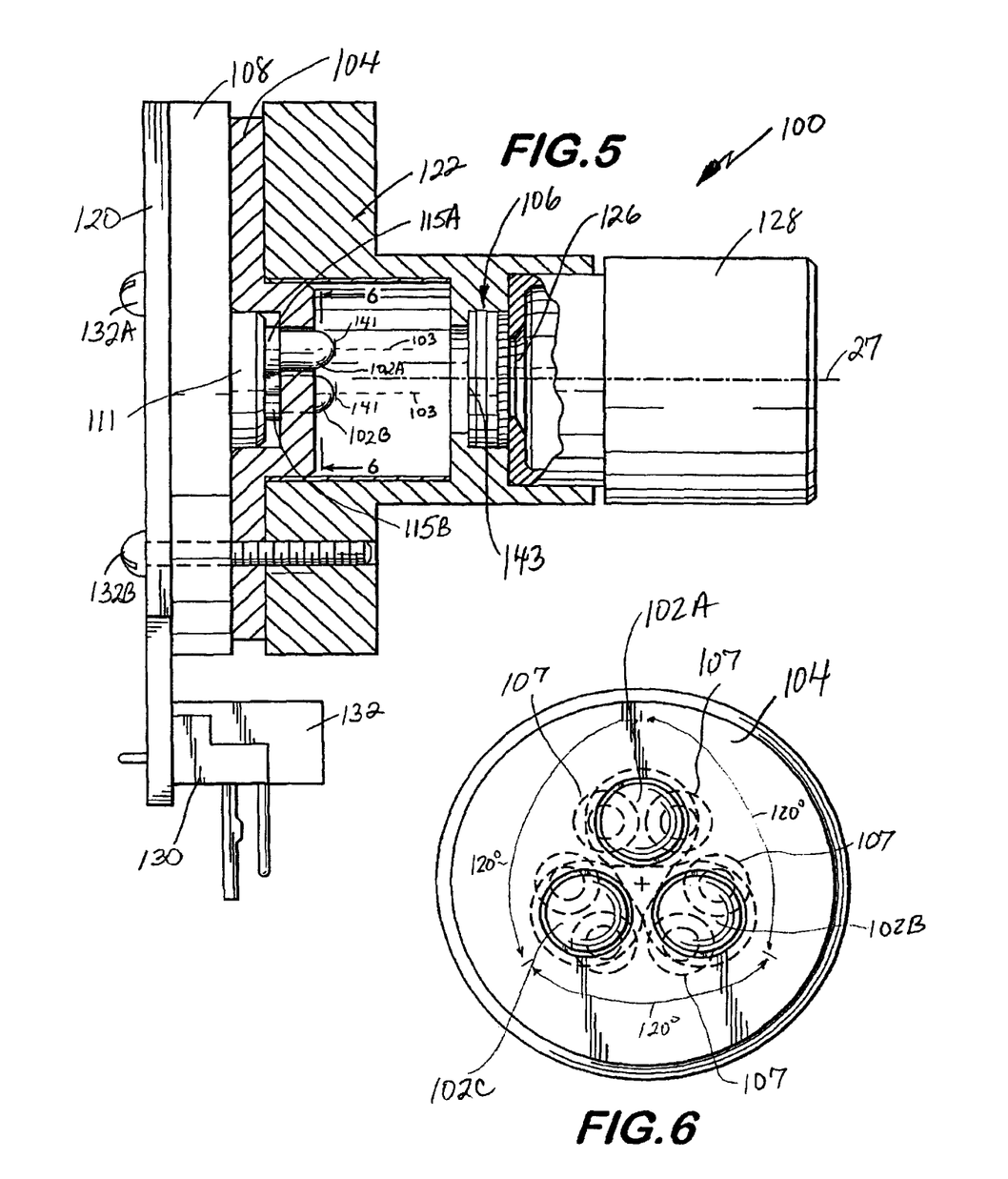
FIG. 5 is side cross-sectional view of the light source taken along line 5—5 of FIG. 3.
FIG. 6 is a view of the light-emitting diode holder taken along line 6—6 of FIG. 5.
Figure 7:
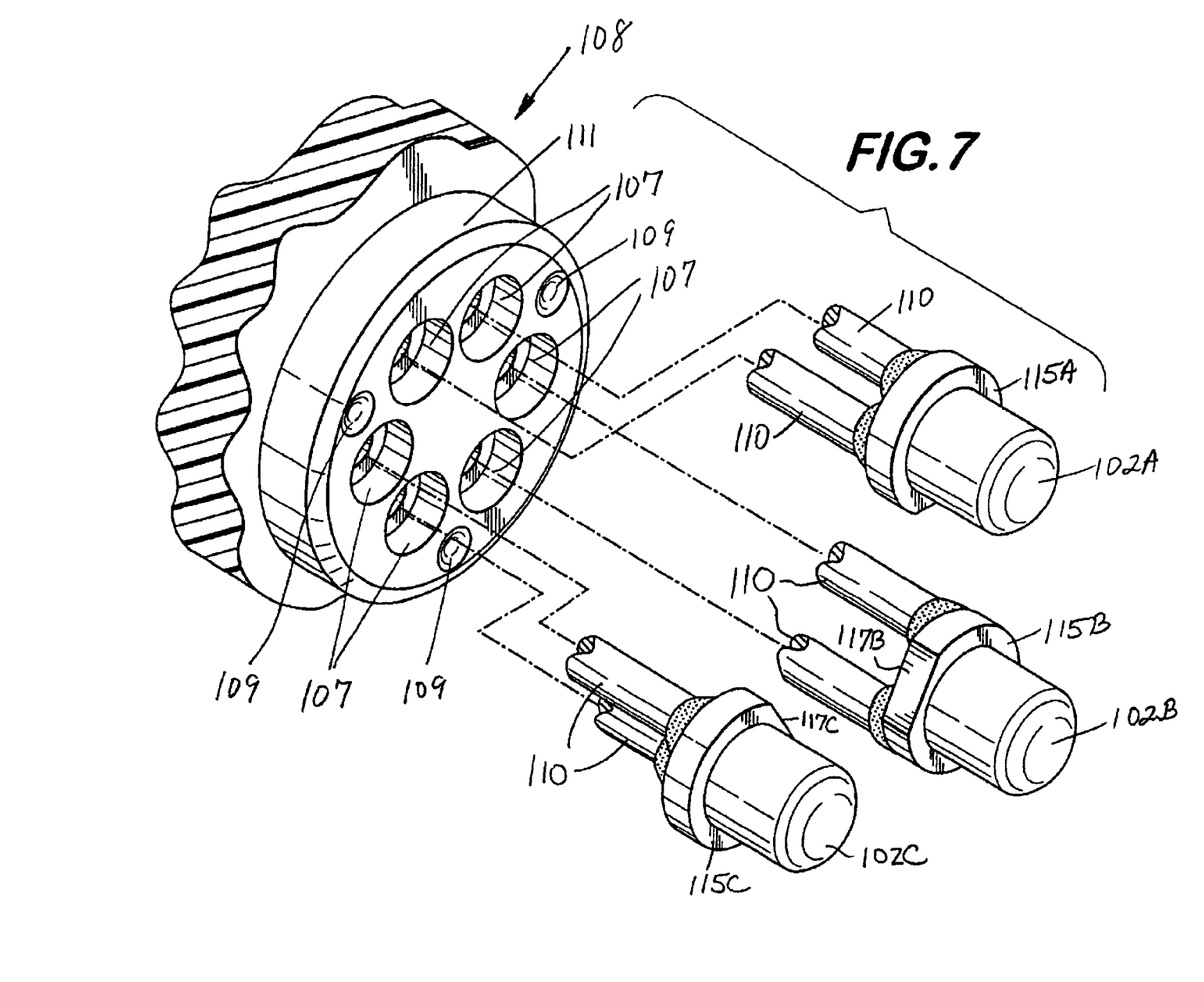
FIG. 7 is an exploded view showing how the light-emitting diodes are properly oriented by lead holes in a clamp plate.
Figure 8:
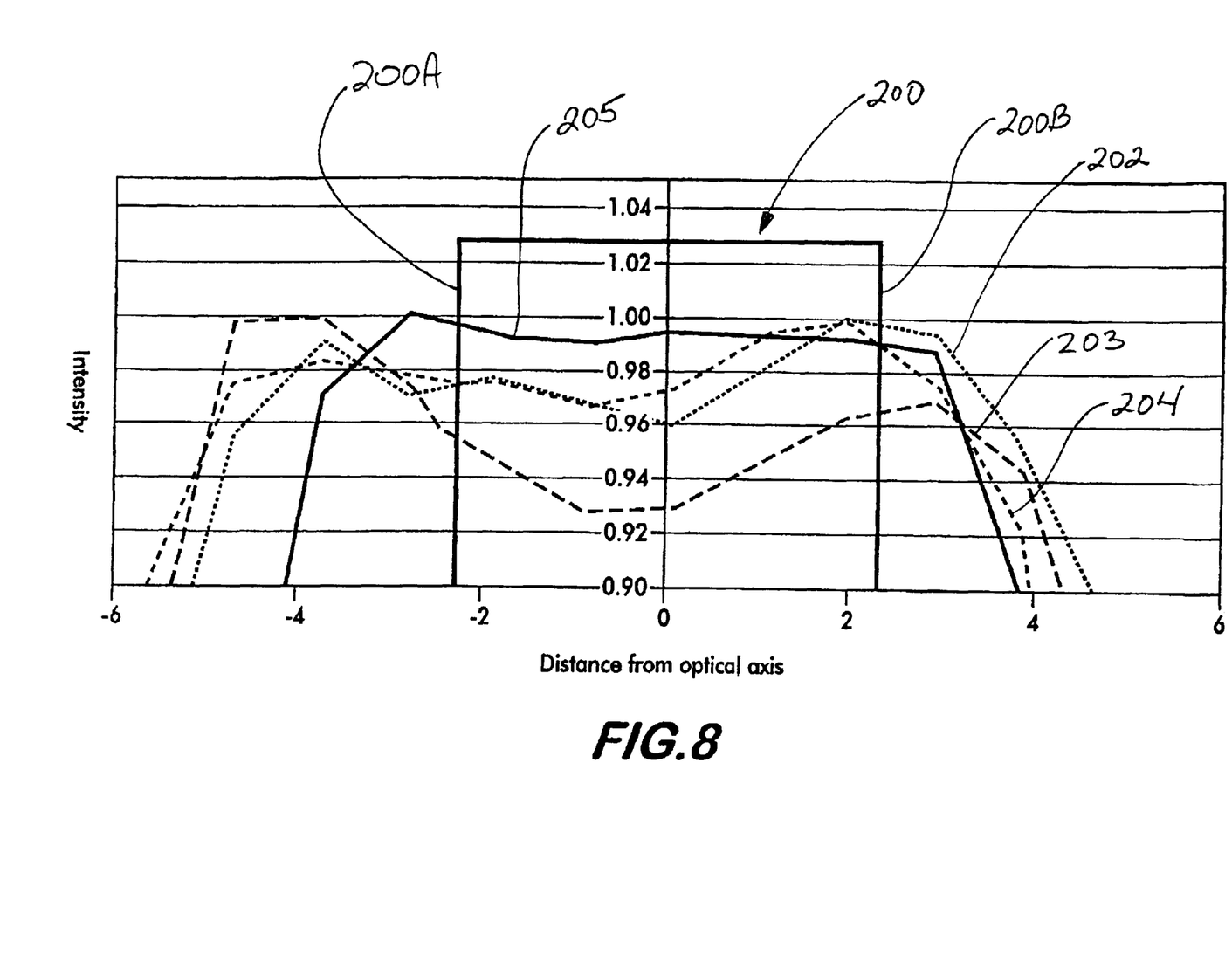
FIG. 8 is a graphical depiction of the light intensity vs. distance from the optical axis of different light emitting diodes and of the light source of the present invention.

As shown most clearly in FIG. 4, the light source 100 basically comprises a plurality (e.g., three) of LEDs 102A–102C (e.g., NSPG320BS LED by Nichia Corp.) positioned in a precision-drilled holder 104, to ensure the LEDs' accurate location, and an optical diffuser 106 to blend the light output of the individual LEDs 102A–102C. In particular, the three LEDs 102A–102C are held in a precisely-determined angular orientation and location by the precision-drilled holder 104 and a clamping plate 108. As shown in FIGS. 5–7, the precision-drilled holder 104 aligns the optical axis 103 (FIG. 5) of each LED 102A–102C so that they are parallel with the optical axis 27 of the transceiver 20 and also mounts the LEDs 102A–102C so that they are positioned 120° with respect to each other (tolerance on each angular position should be <10°); to properly orient these LEDs 102A–102C in the holder 104, a central boss 111 of the plastic clamp plate 108 is fitted over the leads 110 of the LEDs 102A–102C. Holes 107 in the central boss 111 fit tightly to the leads 110 ensuring the each LED 102A–102C is held in the correct angular position around its optical axis 103, with the respective flat sides 117A–117C of collars 115A–115C towards the main optical axis 27. Indicators 109 on the face of the boss 111 ensure that, during assembly, the two leads 110 of any one LED 102A–102C are inserted between two of the indicators 109 for proper LED orientation.

As mentioned earlier, there are symmetrical and asymmetrical inhomogeneities that make the pattern of light from an LED uneven. Symmetrical inhomogeneities in the light emitted by each LED 102A–102C are minimized by ensuring that the LEDs 102A–102C point straight forward, are distributed evenly across the diffuser 106, and placed at the correct distance from it (e.g., 12.5 mm from the front of the LED flange 141 to the inside face 143 of the diffuser 106; FIG. 5). Asymmetrical unevenness (e.g., light beam asymmetry that exists due to the position of the die within each LED package as well as the chip die lead) is minimized by placing each LED 102A–102C at 120° rotation to its neighbor.

The optical (glass) diffuser 106 is mounted in a diffuser holder 122. The inside surface 124 of the holder 122 is polished to so as to reflect any scattered light. The glass diffuser 106 and the polished inside surface 122 together diffuse (e.g., reflect and mix the combined light several times) the light from the three LEDs 102A–102C to form an even, homogeneous, non-directional light source. The finish of the precision-drilled holder 104 and the internal surfaces of the diffuser holder 122 are left as "fine machined" as this provides an increased light output compared to anodizing. A glare shield 128 reduces the amount of scattered light reaching the optical detector (similar to the one shown in FIG. 2) in the transceiver 20. An aperture 126 (FIG. 5) in the glare shield 128 defines the size of the light source 100. The diffuser holder 122 is made from a low-magnesium aluminum alloy which has a low rate of oxidation and the diffuser holder 122 is sealed with silicone rubber during assembly, to prevent the ingress of any gases and therefore maintain the internal surface finish.

Electrical contacts of the LEDs 102A–102C are made by soldering the leads 110 (FIG. 4) of the LEDs 102A–102C to a printed circuit board (PCB) 120. An electrical connector 130 (e.g., a 3-pin Molex connector) couples to an electrical 3-way cable (not shown) that provides electrical power to the light source 100 and a DC/DC (PCB mount) converter 131 (e.g., NME1215S by Newport) is also provided to generate the proper LED excitation. Capacitors C1 and C2 (e.g., 10 $\mu$F, 35V, 20%, tap series) smooth out any remaining ripple from the DC/DC converter 131; the resistors R1 (FIG. 4), R4 and R5 (all zero ohms) are links which are normally set to connect the three LEDs 102A–102C in series with the option to connect them in parallel. Three screws 132A–132C (e.g., M3×14 STL. slot pan/hd) are used to releasably secure the various components to the PCB 120. Retainers 133 and 135 retain mounting screws 137 and 139, respectively, until the light source 100 is ready for installation in the transceiver 20 at which time the retainers 133/135 are discarded.

As mentioned earlier, the transmissometer projects a beam of light 26 across the stack/duct 22. This beam diverges slightly so that its diameter at the plane of the retro-reflector is larger than the reflecting surface. Small movements of the stack/duct 22 structure due to thermal effects, wind, or settling, cause the relative positions of the reflector and the projected beam to move slightly. If the beam does not have precisely the same intensity at all points, there will be a consequent change in the amount of light received at the detector. This will be misinterpreted as a change in the opacity of the gases in the duct.

FIG. 7 shows the variation in light intensity across a single diameter of an opal diffuser placed in front of a conventional LED light source. The box 200 represents a mask placed in front of the opal diffuser screen. Only the portion of the projected light beam between lines 200A and 200B is projected, with the rest being masked off. Lines 202, 203 and 204 are experimental measurements obtained from three different LEDs. Large variations of light intensity are apparent with respect to the distance from the optical axis. In contrast, line 205 shows the effect of placing three LEDs in the angular orientation described above. A dramatic reduction in the variation of intensity across the projected light beam is immediately apparent.

The very small variation in light intensity across the projected light beam results in a consequent small variation of opacity due to misalignment of the transmissometer and retro-reflector. As this is a major component of the total uncertainty of the displayed opacity value, the accuracy of the transmissometer is greatly improved without any reduction in the degree of misalignment which can be tolerated.

Utilizing this improved light source 100 in an opacity monitor results in the following:

enabling the opacity monitors to ensure compliance with opacity limits below 10% as exemplified by 40 C.F.R. §60 Paragraph 650.272 (a) (21) which requires operators of electric arc furnaces to maintain flue gas opacity at or below 3%;

an opacity monitor that can tolerate small movements of the stack/duct structure due to thermal effects, wind, settling, etc. that can cause the relative positions of the retroreflector and the projected light beam to move slightly;

a more evenly illuminated light source, which greatly reduces errors caused by misalignment of the transceiver and retroreflector so that stable, accurate readings can be made at opacity levels below 10%.

a significantly brighter light source which leads to an improvement in the signal-to-noise ratio of the transmissometer.

light source performance is highly repeatable from one opacity monitor to another.

Therefore, as a result of using the light source 100 in the transceiver 20, an opacity monitor is provided that meets what is hereinafter referred to as "specific performance requirements (SPRs)" for ensuring compliance with opacity limits below 10%. These SPRs are defined as all of the requirements of ASTM D6216-98 (a copy of which is attached as APPENDIX) except that the indicated sections of ASTM D6216-98, set forth below, have been amended to include the following changes:

6.4 Insensitivity to Supply Voltage Variations

Permissible drift: a change of less than or equal to 0.2 percent opacity when the main supply voltage is increased or decreased from the nominal voltage by 10 percent.

6.5 Thermal Stability

Permissible drift: a change of less than or equal to 0.2 percent opacity for a 40° F. (22° C.) change in ambient temperature.

6.6 Insensitivity to Ambient Light

Permissible drift: a change of less than or equal to 0.2 percent opacity when exposed to ambient sunlight over the course of a day.

6.8 Zero and Span Calibration

Zero error: 0.2% or less 6.12 Measurement Output Resolution
  Resolution of visual indication: 0.1%
  Resolution of analog output: 0.1%
  Resolution of digital output: 0.1%
7.8 Calibration Error
  ≦1% opacity
7.9 Optical Alignment Indicator
  Opacity monitor, when misaligned, displays a clear indication of that misalignment if the resulting change in opacity is 0.3% or greater.
7.11 Calibration Device Value and Repeatability
  Repeatability: 0.2% or less
  95% confidence limit: 0.3%

Without further elaboration, the foregoing will so fully illustrate our invention that others may, by applying current or future knowledge, readily adopt the same for use under various conditions of service.

We claim:

1. An opacity monitor for measuring the opacity of gases in an open path of gases, said opacity being defined as the fraction of transmitted light which is lost in transmission through the open path of gases, said opacity monitor comprising:
   an optical transmitter having a light source that projects a homogeneous light beam across the open path of gases;
   a reflector for reflecting said homogeneous light beam back towards said optical transmitter through said open path of gases;
   an analyzer for detecting said reflected homogeneous light beam and calculating the opacity of said gases; and
   wherein said opacity monitor detects opacities less than 10 percent while operating within specific performance requirements.

2. The opacity monitor of claim 1 wherein said light source comprises:
   a plurality of light emitting diodes (LEDs) arranged at a predetermined angular orientation with respect to each other and emitting respective light beams therefrom; and
   an optical diffuser positioned at a predetermined distance from said plurality of LEDs for mixing and reflecting said respective light beams to form said homogeneous light beam.

3. The light source of claim 2 wherein said plurality of LEDs comprises three LEDs.

4. The opacity monitor of claim 3 wherein said predetermined angular orientation comprises said LEDs oriented 120° with respect to each other.

5. The light source of claim 4 wherein each of said LEDs comprises a pair of leads and wherein said light source further comprises:
   an LED holder having three holes positioned 120° with respect to each other;
   a clamp member having holes for each one of said leads; and
   wherein said LED holder and said clamp member couple together to maintain said LEDs in said predetermined angular orientation to form said homogeneous light beam.

6. The light source of claim 5 wherein each of said LEDs comprises a flattened portion and wherein said clamp member is arranged to orient the flattened portion of each of said LEDs towards each other.

7. The opacity monitor of claim 5 wherein each of said LEDs comprises a flange and wherein said optical diffuser comprises an inside surface, said predetermined distance comprising 12.5 mm between said LED flanges and said inside surface.

8. The opacity monitor of claim 2 wherein said optical diffuser is supported inside a diffuser holder, said diffuser holder comprising a low-magnesium aluminum alloy.

9. The opacity monitor of claim 8 wherein said optical diffuser is supported by inside surfaces of said diffuser holder, said inside surfaces being fine machined to provide increased light output from said light beams.

10. The opacity monitor of claim 8 further comprising a glare shield coupled to said diffuser holder.

11. The opacity monitor of claim 1 wherein said specific performance requirements comprise all of the requirements of ASTM D6216-98 and including opacity monitoring wherein:
   said opacity monitor exhibits a change of less than or equal to 0.2 percent opacity when a supply voltage to said opacity monitor is increased or decreased from a nominal voltage by 10 percent;
   said opacity monitor exhibits a change of less than or equal to 0.2 percent opacity for a 40° F. (22° C.) change in ambient temperature;
   said opacity monitor exhibits a change of less than or equal to 0.2 percent opacity when exposed to ambient sunlight over the course of a day;
   said opacity monitor exhibits a zero error of 0.2 percent or less;
   said opacity monitor exhibits:
     (a) a resolution of visual indication of 0.1 percent;
     (b) a resolution of analog output of 0.1 percent;
     (c) a resolution of digital output of 0.1 percent;
   said opacity monitor exhibits a calibration error of less than or equal to 1 percent opacity;
   said opacity monitor, when misaligned, displays an indication of that misalignment if a resulting change in opacity is 0.3 percent or greater; and
   said opacity monitor exhibits a calibration device repeatability of 0.2 percent or less.

* * * * *